United States Patent [19]

Carlson, Jr.

[11] 4,373,147

[45] Feb. 8, 1983

[54] TORQUE COMPENSATED ELECTRIC MOTOR

[75] Inventor: William L. Carlson, Jr., St. Cloud, Minn.

[73] Assignee: General Signal Corporation, Stamford, Conn.

[21] Appl. No.: 286,297

[22] Filed: Jul. 23, 1981

[51] Int. Cl.³ .............................................. H02P 5/52
[52] U.S. Cl. ......................................... 318/48; 73/59;
 318/659; 318/436; 318/49; 310/112; 310/114
[58] Field of Search ............... 73/59; 318/48, 49, 659,
 318/676, 488, 660, 469, 648, 456, 457, 689, 436;
 325/229–231; 310/112, 29, 36, 114–116

[56] References Cited

U.S. PATENT DOCUMENTS

| | | |
|---|---|---|
| 912,144 | 2/1909 | Mavor . |
| 1,983,896 | 12/1934 | Bottcher . |
| 3,089,044 | 5/1963 | Bolton .................................. 310/36 |
| 3,343,405 | 9/1967 | Gilinson et al. ....................... 73/59 |
| 3,357,003 | 8/1944 | Hurndall ............................... 73/59 |
| 3,586,938 | 6/1971 | Le Gall ................................. 318/49 |
| 3,683,249 | 8/1972 | Shibata . |
| 3,722,262 | 3/1973 | Gilinson, Jr. et al. ................. 73/59 |
| 3,950,430 | 8/1960 | Katz ................................... 318/689 |
| 4,126,818 | 11/1978 | Taylor . |

Primary Examiner—David Smith, Jr.
Attorney, Agent, or Firm—Leitner, Palan, Martin & Bernstein

[57] ABSTRACT

An electric motor having a first rotor on an output shaft, a first stator pivotally mounted to a housing, a second rotor mounted to the first stator and a second stator mounted to the housing. The second stator is driven with a control signal which is a function of the measure reaction torque experienced by the first stator to produce a counter torque to balance the reaction torque. A consistency transmitter mounted on the output shaft produces torque on the first stator as a function of the consistency of the material in which it is rotated.

14 Claims, 5 Drawing Figures

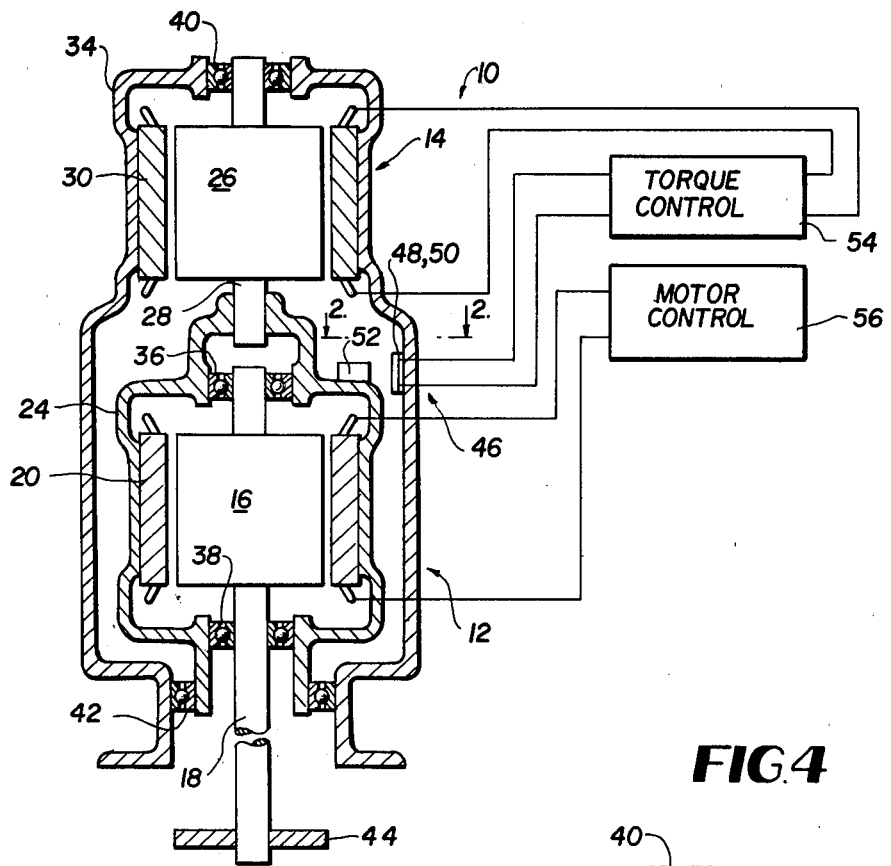
FIG.1
FIG.4
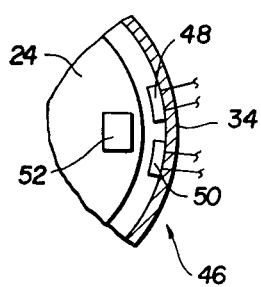
FIG.2

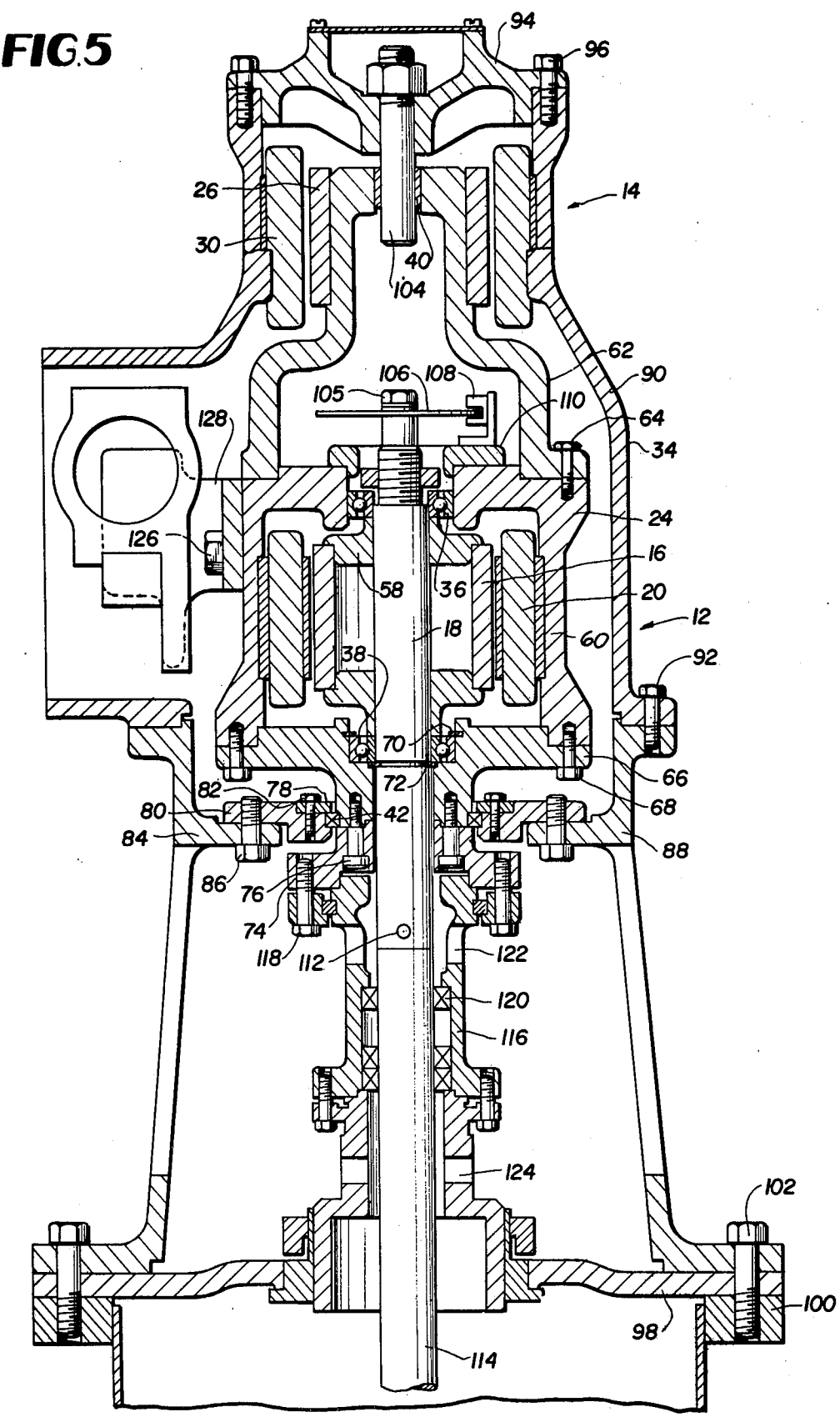

TORQUE COMPENSATED ELECTRIC MOTOR

BACKGROUND OF THE INVENTION

The present invention relates generally to torque compensated electric motors and more specifically to their use with rotary consistency transmitters.

Consistency transmitters generally involved an element which is moved relative to the material whose consistency it is to measure. The transmitter senses increased drag in the relative motion between the material and the sensor. This increased drag is a function of the consistency of the material and may be interpreted by appropriate circuitry and provided as an output indication. One type of consistency transmitter is a rotary consistency transmitter wherein a sensor is rotated in the material whose consistency is to be determined. Typically the sensor is rotated by an electric motor. With an increase in the consistency of the material to be sensed, the drag on the sensor is increased. This drag will create a back torque or reaction torque in the stator of the motor. By measuring the reaction or back torque, the consistency of the material is determined.

In prior art rotary consistency transmitters, the stator of the drive motor is free to rotate in response to the back torque or the reaction torque. A torque arm is provided extending radially from the stator. The position of the arm is monitored as an indication of reaction torque. The system is brought into an equilibrium by one of two methods (a) a force balance or (b) a zero displacement. In the force balance system, a counter force is provided to stop the rotation of the torque arm. In the zero displacement, the torque arm is rotated back to a zero displacement position and held at that position. The prior art has sensed the position of the torque arm pneumatically or electrically and has provided in the pneumatic system a bellows to provide the appropriate counter torque. In the electrical system, a linear variable differential transformer has been used to monitor the position of the torque arm and an electric force motor has been used to produce the counter torque. In both these systems, the counter torque producing mechanism is not symmetrical about the axis of rotation of the motor and thus results in undesirable radial forces on the structure which supports the motor.

SUMMARY OF THE INVENTION

An object of the present invention is to provide a symmetrical torque compensation control system for an electric motor.

Another object of the present invention is to provide a torque compensated electric motor for use in a rotary consistency transmitter.

Still another object of the present invention is to provide a compact and economical torque compensator electric motor.

Still even a further object of the present invention is to provide a torque compensated electric motor which is economical and may be used in a rotary consistency transmitter.

These and other objects of the invention are attained by mounting a first stator of a first motor and a second rotor of a second motor to a cage which is rotatably mounted to a housing and mounting a second stator to the housing concentric to the second stator. Means are provided to measure the reactional torque experienced by the first stator and to provide a control signal to the second stator as a function of the measured torque to produce a counter-torque in the second rotor to balance the reactional torque experienced by the first stator. The measuring means measures the angular displacement of the first stator from a predetermined position and the control signal is provided to halt the rotation of the first stator or to maintain the first stator at the predetermined position. The second rotor and stator comprise a second electric motor having an electrical torque capacity at least equal to that of the first rotor and stator which comprise a first motor. The second motor may be either concentric to or coaxial with the first motor and thus provides a symmetrical torque compensation system. A sensor may be mounted to the end of the output shaft to which the first rotor is connected for producing a torque on the first stator as a function of the consistency of the material in which the transmitter sensor is rotated. Thus, the consistency is determined by the torque produced in the first stator.

Other objects, advantages and novel features of the present invention will become apparent from the following detailed description of the invention when considered in conjunction with the accompanying drawings.

BRIEF DESCRIPTION OF THE DRAWINGS

FIG. 1 is a schematic representation of a torque compensated electric motor incorporating the principles of the present invention.

FIG. 2 is a partial view taken along lines 2—2 of FIG. 1 illustrating the torque sensor incorporating the principles of the present invention.

FIG. 4 is a schematic representation of a second electrically torque compensated electric motor incorporating the principles of the present invention.

FIG. 5 is a detail cross-sectional view of an electrically torque compensated electric motor incorporating the principles of the present invention.

DESCRIPTION OF THE PREFERRED EMBODIMENTS

Figure 3:
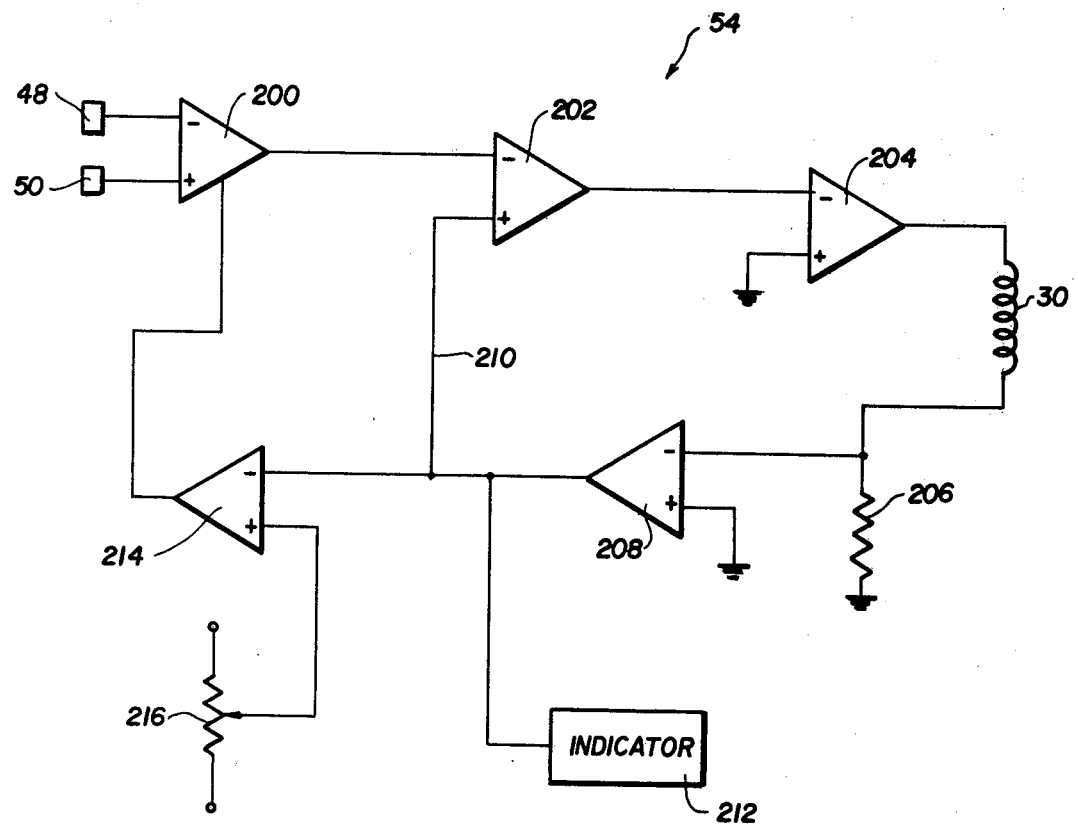
FIG. 3 is an electrical diagram of a torque control circuit.

An electrically torque compensated electric motor 10 as illustrated in FIG. 1 includes a first motor 12 and a second motor 14. The first motor 12 includes a first rotor 16 mounted to an output shaft 18 and a first stator 20 mounted to the interior of a cage 24 concentric to the first rotor 16. The second motor 14 includes a rotor 26 mounted to a shaft 28 which is mounted to the cage 24 of the first stator 20. Concentric to the second rotor 26 is a second stator 30 mounted to the interior of motor housing 34. The output shaft 18 is mounted to the interior of the cage 24 by bearings 36 and 38 so as to rotate relative thereto. Shaft 28 is connected through bearing 40 to the housing 34 and the cage 24 is connected to the housing 34 by bearings 42. Thus, it can be seen that the rotor 16 and output shaft 18 rotate relative to the cage 24 and the cage 24 and shaft 28 rotate relative to the housing 34.

A consistency sensor 44 is shown mounted to the end of the shaft 18 which extends exterior to the housing 34. This consistency sensor may be a disc, blade or other device which is well known in rotary consistency transmitters. A reaction or back torque sensor 46 is mounted to the interior of the housing 34. The torque sensor 46 senses the movement of the first stator 20 relative to the housing such that a torque control circuit 54 may provide an appropriate signal to stop the movement in a force balance system or to return the stator to a zero displacement position and maintain it there in a zero displacement type system. One example of a torque sensing system is illustrated in detail in FIG. 2 and includes a pair of Hall-effect transducers 48 and 50 mounted to the interior of the housing 34 and a magnet 52 mounted to the exterior of cage 24. The back or reaction torque experienced by the first stator 20 causes a rotational displacement of the cage 24 so as to move the magnet 52 relative to the housing 34 and the pair of fixed Hall-effect transducers 48 and 50. A torque control 54 senses the output of the pair of Hall-effect transducers 48 and 50 and provides a signal to the second stator 30 which causes an angular rotation of the second rotor 26 to produce a counter-torque to the first stator 20 through shaft 28 and cage 24. In a zero displacement system, the counter-torque is applied until Hall-effect transducers 48 and 50 sense a predetermined position of the magnet 52. Preferably this predetermined position is where the magnet 52 is equally distant from the Hall-effect transducers 48 and 50. In a force balance system, the counter torque is applied until no motion is sensed by the Hall-effect transducers 48 and 50.

Thus, the torque control 54 produces a counter-torque equivalent to the torque experienced by the first stator 20 so as to keep the first stator 20 in equilibrium. Although Hall-effect transducers and magnets are shown as the torque sensor 46, other devices may be used, for example, a light source and photocell. Although the Hall-effect transducers and magnets are the preferred embodiments they require a minimum amount of space and thus are economically efficient.

A motor control circuit 56 provides signals to the stator 20 for a desired rotational speed of output shaft 18. Since motor controls are well known and do not form part of the present invention it will not be described here in detail.

When the electrically torque compensated electric motor of the present invention is used as a rotary consistency transmitter, the material in which the consistency sensor 44 is rotated provides a drag on the output shaft 18 and the rotor 16. This drag produces an increased reaction torque in the first stator 20. This torque is sensed by the torque control circuit 54 which produces a counter-torque to balance the reaction torque. The amount of measured reaction torque is an indication of the consistency of the material in which the consistency sensor 44 rotates. Thus the signal of the torque control circuit 54 may be used and transmitted to additional circuits which will indicate the consistency of the material.

An example of a torque control circuit 54 for a force-balance system is illustrated in FIG. 3. The output of the Hall-effect transducers 48 and 50 are connected to the negative and positive terminals, respectively, of input differential amplifier 200. The output of the input differential amplifier 200, which indicates a position error, is connected to the negative input of motor current differential amplifier 202. The output of the motor current differential amplifier 202 is connected to a driver amplifier 204. The torque motor 30 is driven with the output of the driver amplifier 204 and the current through the torque motor is sensed by current sense resistor 206. A current sense amplifier 208 is connected to the current sensor resistor 206 and provides a signal indicative of the current through the torque motor 30. This sensed current is provided via line 210 to the positive input of the motor current differential amplifier 202.

The sensed current at the output of amplifier 208, which is the compensation torque, is provided to an indicator 212. The current through the torque motor 30 from the output of amplifier 208 is also provided to the negative input of a current limiter differential amplifier 214. The positive input is connected to an adjustable current limiting resistor 216. The output of the current limiter 214 is provided to adjust the gain of the input differential amplifier 200. Thus for large current signals to the torque motor 30, the gain of the input amplifier 200 is reduced to limit the size of the current to drive the torque motor.

The input amplifier 200 of FIG. 3 senses a position error from the Hall-effect transducers 48 and 50 and provides an error current to the input of motor current amplifier 202. The current from the motor current amplifier 202 through driver amplifier 204 builds up slowly through the torque motor 30 and provides a slow buildup of the feedback signal on line 210 to the positive input of differential amplifier 202. Thus, the output of differential amplifier 202 and the current to the torque motor 30 slowly decreases until the current on the output of differential amplifier 202, through the motor 30 and fed back to line 210 are all equal to approximately one-half the position error signal from the input amplifier 200. This will establish an equilibrium condition in the loop including differential amplifiers 202 and 204, motor 30 and sense amplifier 208. This circuit is but an example of a torque control circuit 54 for a force balance system.

In FIG. 1, the second motor 14 is illustrated as axially aligned and displaced from the first motor 12. FIG. 4 illustrates the concept of the present invention incorporated wherein the second motor 14 is concentric to the first motor 12. The rotor 26 of the second motor 14 is mounted directly to the cage 24 concentric to the first stator 20 and the first rotor 16. The second stator 30 which is still mounted to the housing 24 is concentric to the first rotor 16, the first stator 20, and the second rotor 26. The housing 34 is modified to accommodate the concentric arrangement of the motors 12 and 14 versus the axial arrangement of FIG. 1.

In both the embodiments of FIG. 1 and FIG. 4, the torque compensation system including the second motor 14 is symmetrical about the axis of rotation of the first motor 12 and thus does not produce any of the undesirable forces of the prior art systems. It should be noted that the second motor 14 should have an electrical torque capacity equal to or greater than the first motor 12 in order to provide effective counter torque. In this regard, the axial arrangement of FIG. 1 is preferred in that the first motor 12 and the second motor 14 may be the same motor obtained from the same manufacturer. Only an interconnecting element need be provided so as to connect the rotor of the second motor to the stator of the first motor.

A detailed illustration of a torque compensated electric motor is illustrated in FIG. 5. The first rotor 16 is shown mounted directly to output shaft 18 by a core 58. The cage 24 includes a generally cylindrical casing 60 having a first extension 62 extending from the top thereof and secured thereto by fastener 64 and a bottom 66 secured to the casing 60 by fastener 68. The first stator 20 is mounted directly to the interior of casing 60. The bearing 36 interconnects the top of shaft 18 and core 58 to the interior of casing 60. The bearing 38 interconnects the other end of the output shaft 18 and the core 58 to the interior of the bottom 66 and is maintained in place between a pair of snap rings 70 and 72. The bearings 36 and 38 are ball bearings capable of operating at a rotational speed of approximately 250 rpm between the stator 20 and the rotor 16.

Bearing 42 has one race connected to the exterior of cage 24 between the bottom plate 66 and an annular clamp 74 secured to the bottom 66 by a fastener 76. The other race of bearing 42 is clamped to the interior of the housing 34 by a ring 78 which is secured to an annular clamp 80 by fastener 82 which is secured to an annular ledge 84 by fastener 86. The bearing 42 is a torque tube bearing of high precision and capable of resisting substantial axial forces. The specific connection of the races to the housing 34 and the cage 24 provides resistance to axial motion. It should also be noted that the axis of the output shaft 18 and the motors 12 and 14 is vertical. Thus, the bearing 42 supports the weight of the output shaft 18, first rotor 16, first stator 20, carriage 24 and second rotor 26.

The housing 34 includes a mounting base 88, a cover 90 maintained to mounting base 88 by fastener 92, and a cap 94 fastened to the cover 90 by fasteners 96. A bottom plate 98 and annular ring 100 are secured to the bottom of the base 88 by fasteners 102.

Extending into the interior of the housing 34 through the cap 94 is a post 104. Bearing 40 interconnects the top extension 62 of the carriage 24 to the post 104. The bearing 40 is a roller bearing or sleeve bearing and is preferably a needle bearing with a race connected to the interior of the extension 62 of the carriage 24 and the outer surface of post 104 forming the other race. This bearing relationship between the post 104 and the extension 62 of the cage 24 maintains axial alignment of the cage relative to the housing at the top rotational connection. Thus, between bearing 40 and 42, the carriage 24 is rotatably connected, supported vertically and maintained axially aligned. It should be noted that the bearing 40 is critical in that it maintains the axial alignment without bringing radial forces to bear on the carriage 24 due to loading of the output shaft 18. The second rotor 26 is mounted directly to the exterior of the extension 62 and the second stator 30 is mounted directly to the interior of the cover 60 of the housing 34.

It should be noted that casing 60 and the interconnection of the output shaft 18, rotor 16 and stator 20 may be that of a standard available motor. The extension 62 is specially designed and attached to the standard casing 60. Similarly, the bottom 66 of the casing 60 may be modified to include the connection of the bearing 42 to the exterior surface of the cage so that they can be pivotally interconnected to the housing 34.

Mounted to the top of output shaft 18 by fastener 105 is a slotted disc 106. One of three sensors 108 is positioned around the periphery of slotted disc 106 and is mounted to the casing 60 by an adjustable ring 110. The three sensors 108 sense the slots in the slotted disc 106 and provide three timing signals for three phase operation of the first motor 12 including stator 20 and rotor 16.

Connected to the other end of output shaft 18 is a second or external shaft 114 to which may be connected a consistency sensor. Encompassing a portion of the external shaft 114 is an extension 116 which is connected to the cage 24 via fastener 118 received in annular clamp 74. Seals 120 extend between the interior of the extension 116 and the external output shaft 114. Apertures 122 in the extension 116 provide access to the interconnection of shafts 18 and 114. Mounted between the bottom plate 98 of the housing 24 and the extension 116 of the cage 24 is a rubber flexure or torsional resilient element 124. The rubber flexure member 124 permits limited axial and rotational movement of the cage 24 relative to the housing.

From the preceding description of the preferred embodiments, it is evident that the objects of the invention are attained in that a new improved electrically torque-compensated electric motor is provided. Although the invention has been described and illustrated in detail, it is to be clearly understood that the same is by way of illustration and example only and is not to be taken by way of limitation. The spirit and scope of this invention are to be limited only by the terms of the appended claims.

What is claimed:

1. A torque compensated electric motor comprising:
a housing;
an output shaft extending from said housing;
a first rotor mounted to said output shaft in said housing;
a first stator rotatably mounted in said housing concentric to said first rotor;
a second rotor mounted in said housing to said first stator for rotation therewith;
a second stator mounted in said housing concentric to said second rotor;
means for measuring the reaction torque experienced by said first stator; and
control means for providing a control signal to said second stator as a function of said measured torque to produce a counter-torque in said second rotor to balance the reaction torque experienced by said first stator.

2. A torque compensated electric motor according to claim 1 wherein said measuring means measures the angular motion of said first stator and said control means provides said control signal to halt said angular motion of said first stator.

3. A torque compensated electric motor according to claim 1 wherein said measuring means includes a magnet and a Hall-effect transducer, one mounted to said first stator and the other to said housing, for measuring the angular displacement of the first stator relative to said housing.

4. A torque compensated electric motor according to claim 1 wherein said measuring means measures the angular displacement of said first stator from a predetermined position and said control means provides said control signal to maintain said first stator at said predetermined position.

5. A torque compensated electric motor according to claim 1 wherein said second rotor is displaced axially from said first stator.

6. A torque compensated electric motor according to claim 1 wherein said second rotor is concentric to said first stator.

7. A torque compensated electric motor according to claim 1 wherein said second rotor and stator have at least equal electric torque capacity as the first rotor and stator.

8. A rotary consistency transmitter comprising;
a housing;
an output shaft extending from said housing;
a first rotor mounted to said output shaft in said housing;

a first stator rotatably mounted in said housing concentric to said first rotor;

a second rotor mounted in said housing to said first stator for rotation therewith;

a second stator mounted in said housing concentric to said second rotor;

means for measuring the reaction torque by said first stator;

control means for providing a control signal to said second stator as a function of said measured torque to produce a counter-torque in said second rotor to balance the reaction torque experienced by said first stator; and transmitter means mounted to the end of said output shaft exterior said housing for producing a torque on said first stator as a function of the consistency of material in which said transducer means is rotated.

9. A rotary consistency transmitter according to claim 8 wherein said measuring means measures the angular displacement of said first stator from a predetermined position and said control means provides said control signal to maintain said first stator at said predetermined position.

10. A rotary consistency transmitter according to claim 8 wherein said second rotor is displaced axially from said first stator.

11. A rotary consistency transmitter according to claim 8 wherein said second rotor is concentric to said first stator.

12. A rotary consistency transmitter according to claim 8 wherein said second rotor and stator have at least equal electric torque capacity as the first rotor and stator.

13. A torque compensated electric motor according to claim 8 wherein said measuring means measures the angular motion of said first stator and said control means provides said control signal to halt said angular motion of said first state.

14. A torque compensated electric motor according to claim 8 wherein said measuring means includes a magnet and a Hall-effect transducer one mounted to said first stator and the other to said housing, for measuring the angular displacement of the first stator relative to said housing.

* * * * *